United States Patent [19]

Schweblin

[11] Patent Number: 4,639,248
[45] Date of Patent: Jan. 27, 1987

[54] SYRINGE

[76] Inventor: Jean-Denis Schweblin, 4, Place de l'Etrier, 1224 Chene Bougeries, Switzerland

[21] Appl. No.: 801,057

[22] Filed: Nov. 22, 1985

[30] Foreign Application Priority Data

Dec. 7, 1984 [CH] Switzerland ............... 5832/84
Jan. 11, 1985 [CH] Switzerland ............... 123/85

[51] Int. Cl.⁴ ............................................. A61M 5/00
[52] U.S. Cl. ..................................... 604/187; 604/218; 604/227; 128/765
[58] Field of Search ............. 604/187, 227, 232, 224, 604/218, 208; 128/765, 766

[56] References Cited

U.S. PATENT DOCUMENTS 3,325,061 6/1967 Ellsworth ........................... 604/218
3,990,446 11/1976 Taylor ................................ 604/227
4,484,915 11/1984 Tartaglia ........................... 604/227

Primary Examiner—John D. Yasko
Attorney, Agent, or Firm—Kane, Dalsimer, Kane, Sullivan and Kurucz

[57] ABSTRACT

The syringe for taking and emptying a liquid comprises a cylindrical body and a piston actuated by means of a piston rod movable coaxially in the body for sucking or ejecting a liquid through a needle-carrying nozzle. This body is provided with a first bearing surface of approximatively semi-cylindrical cross-section. The piston is attached through its rod to a second bearing surface. By moving the second bearing surface toward the first bearing surface, the volume of the inner chamber of the cylindrical body increases, whereas moving the second bearing surface away from the first bearing surface will decrease the volume of this chamber.

8 Claims, 9 Drawing Figures

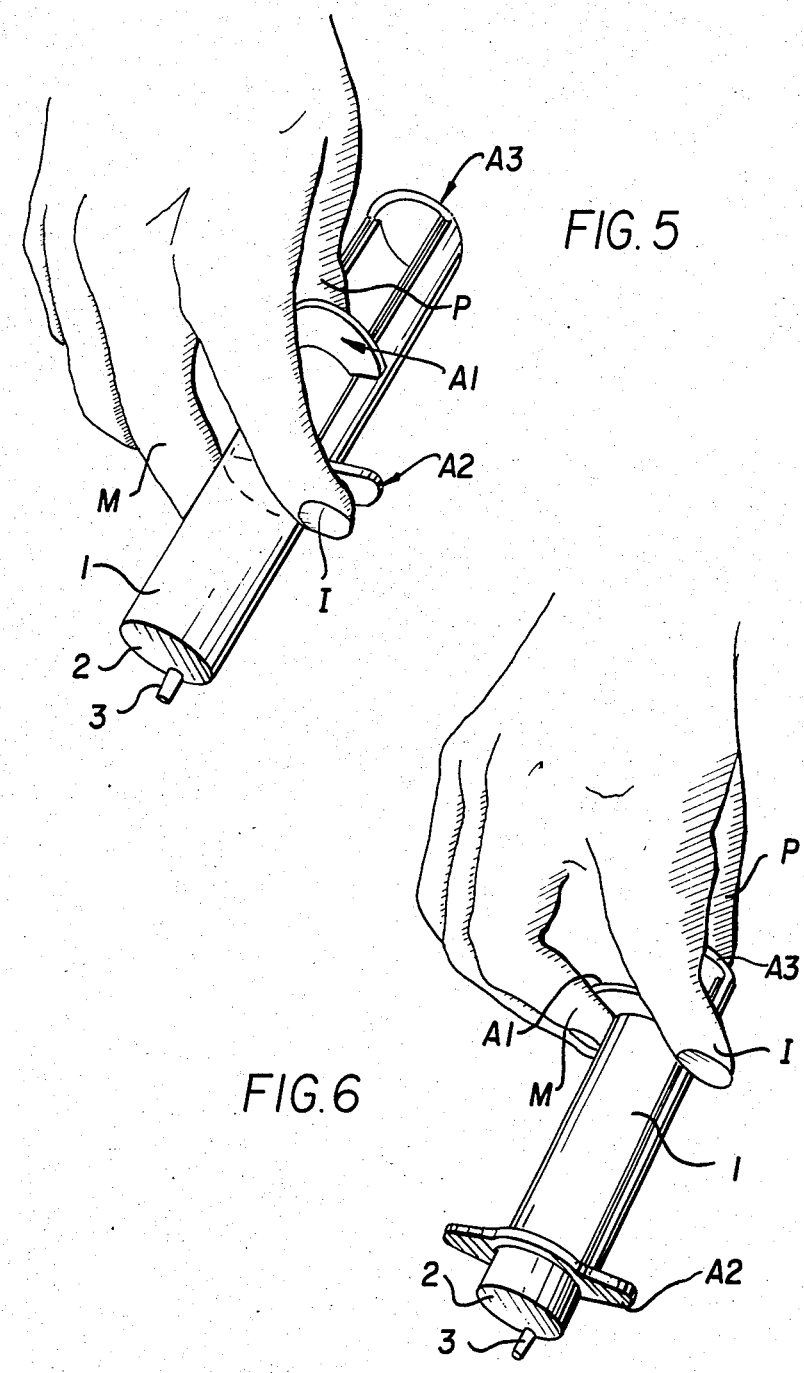

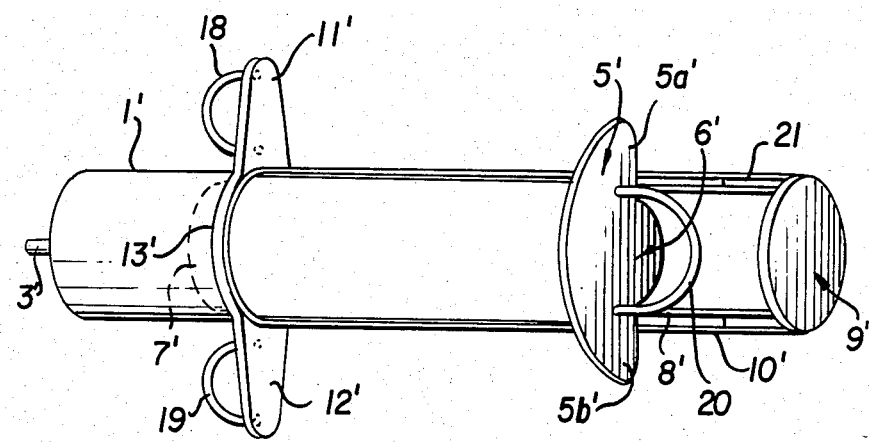
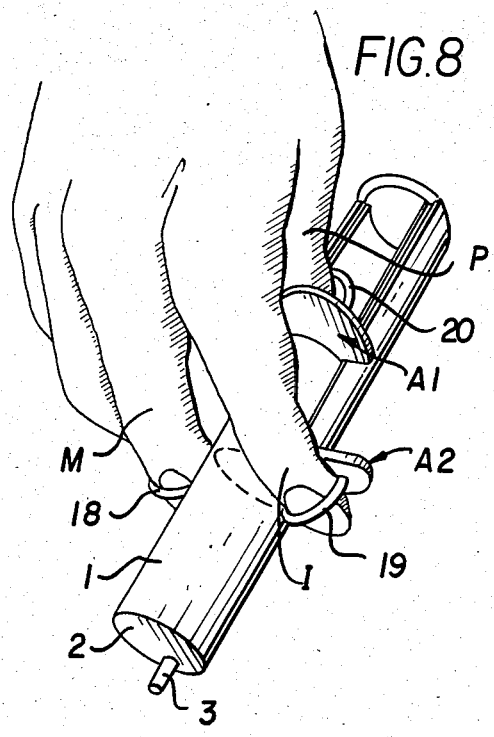
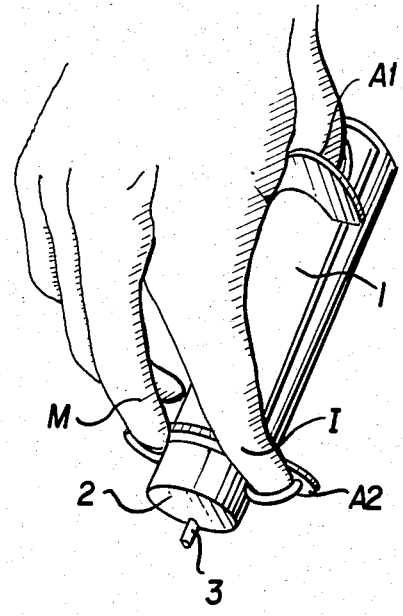

SYRINGE

FIELD OF INVENTION

The present invention relates to a syringe for extracting and emptying a liquid, which comprises a cylindrical body provided on its closed front end with a needle supporting nozzle, and a piston movable coaxially in said body, so that a relative axial movement between the body and the piston will correspond to a variation in the volume of the chamber formed between the front end of the body, its cylindrical wall and the adjacent surface of the piston, for sucking or ejecting a liquid through said needle supporting nozzle.

PRIOR ART

Hitherto known syringes used for taking and emptying liquids are generally of the type wherein the piston detachably and slidably fitted in the cylindrical body is adapted to be pulled out from this body by means of the piston rod, the action exerted on the syringe consisting in moving the piston rod away from the cylindrical body. This type of syringe, existing in both throw-away and re-usable versions, that is, the version in which the syringe is disposed of after one use and the version in which the syringe is re-used after sterilization, is attended by three major inconveniences. Firstly, this known syringe requires the use of both hands for taking the fluid, one hand holding the syringe body while the other hand holds the front end of the piston. As the suction movement is accomplished, the operator's hands are moved away from each other and consequently their coordination is detrimentally affected and becomes inaccurate. Secondly, the position of the syringe on the body from which the fluid is to be taken is uneasy because the hand holding the syringe body is more or less on the way with respect to the patient's body.

Thirdly, the puncture and the taking of fluid by the syringe must take place in two steps during which the positions of the hands are modified. In a first step, one hand holds the patient's body and the other hand holds the syringe to introduce the needle into the body. In the second step, the hand holding the patient's body grips the cylindrical body of the syringe and the hand which previously held the syringe will grip the head or tip of the piston rod in order to pull the piston away from the patient's body and take the fluid therefrom. Consequently, both hands are necessarily involved in the handling of the syringe.

To avoid the difficulty of operating known syringes with a single hand, notably in the fluid-taking function, a known proposition consisted in providing at the rear end of the piston rod a ring adapted to be engaged by the operator's thumb. However, the force required for taking the fluid, including the frictional resistance exerted by the piston on the inner wall of the cylindrical body of the syringe, is frequently such that the thumb is unable to perform the necessary step or the resulting tension tends to interfere with the syringe movements, at the expense of the precision of the operation.

Other solutions have been proposed with a view to facilitate the fluid taking operation and also, to a minor extent, the emptying or injection operations of the syringes. It was found that these propositions involved complications in the syringe construction and therefore increased its cost, without mentioning the undesired changes in the operator's habits, which may even lead to handling errors.

The searches made among prior art have also shown such apparatus as described in the U.S. Pat. No. 4,263,911 and 4,484,915, where the fundamental idea of collecting a liquid by bringing together two opposite bearing surfaces connected one to the syringe body and the other one to the piston is disclosed. Such constructions are relatively complex. In the first cited patent, however, the use of the proposed syringe requires the two hands of the operator. In the second patent cited, the actuating organs are exterior and auxiliary to a normal type syringe which they complete. The number of the required parts increased the cost of the whole syringe. The axis along which the pressure is exerted is clearly diagonal with the axis of the syringe itself. The rigidity and the strength of the sliding parts are obtained at the expenses of an increase of weight of the whole syringe and of a more complicate adjustments of the part with respect to each other.

SUMMARY OF THE INVENTION

It is the primary object of the present invention to provide a syringe free of the above-described inconveniences, notably in its fluid-taking functions, but also in its emptying or injection functions, this improved syringe being of very simple construction, extremely accurate in actual use and departing only very slightly from the habits acquired with conventional syringes. This improved syringe can be handled single-handed, without any change of position between the fluid taking function, the emptying function, possibly the injection function, and without requiring any particular effort for the fingers of the operator's hand.

The syringe according to the present invention is characterized by the fact that its body comprises at its rear end a first bearing surface and that the piston is rigid through its rod being coaxial and of approximately semi-cylindrical cross-section, with a second bearing surface located between the first bearing surface and the front end of said body, so that when the second bearing surface is moved toward the first bearing surface the volume of the inner chamber increases, whereas when said second bearing surface is moved away from the first bearing surface the volume of said chamber decreases.

BRIEF DESCRIPTION OF THE DRAWINGS

The accompanying drawings illustrate diagrammatically by way of example three forms of embodiment of the invention.

FIG. 5 is a perspective view of the syringe according to the first form of embodiment, during its actuation for taking a fluid from a body;

FIG. 6 is a view similar to FIG. 5, showing the actuation of the syringe for emptying purposes;

FIG. 7 is a perspective view showing the third form of embodiment;

FIG. 8 is a perspective view showing the syringe according to the third form of embodiment, actuated during a taking operation, and FIG. 9 is a view similar to FIG. 8 showing the syringe being actuated during a emptying operation.

DESCRIPTION OF THE PREFERRED EMBODIMENTS

In the following description, the syringe portions located on the side of the needle-supporting nozzle as disclosed hereinafter are referred to a "front" component elements or parts, and the syringe portions disposed at the other end of the syringe, i.e. adjacent the piston rod as disclosed hereinafter, are referred to as the "rear" component elements.

Figure 1:
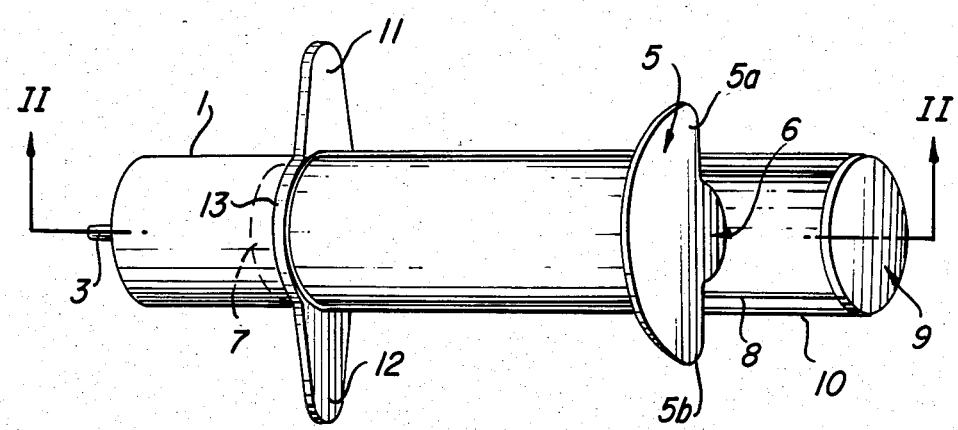
FIG. 1 is a perspective view showing a first form of embodiment.
Figure 2:
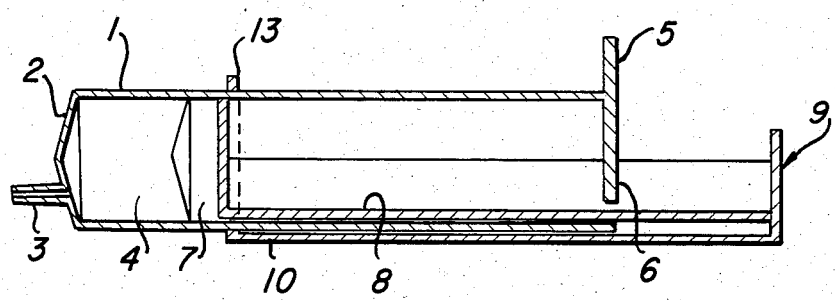
FIG. 2 is a longitudinal section taken along the line II—II of FIG. 1.

Referring first to FIGS. 1 and 2, it will be seen that the syringe comprises a cylindrical body 1 having its front end 2 closed by a wall perpendicular to the cylinder axis and provided with a needle-supporting nozzle 3 in which a passage (not shown) is formed for connecting the inner chamber 4 to the atmosphere. The opposite end of the cylindrical body 1 is partially covered by a first bearing surface consisting of a substantially semi-circular plate 5 having a diameter greater than that of said body 1 and provided preferably with an inner semi-circular extension 6 of smaller diameter.

A piston 7 of conventional type is slidably fitted in the cylindrical body 1 and defines the variable volume of chamber 4. This piston is connected to a rigid internal piston rod 8 having in cross-section the shape of a cylinder portion of a diameter slightly smaller than the inner bore diameter of said body 1.

At its rear end, this rod 8 is capped by a circular plate 9 constituting the third bearing surface of a diameter slightly greater than the outer diameter of said body 1 and having an extension toward the front portion of body 1 in the form of a second semi-circular outer portion 10 covering the body 1 and ending substantially at the level of said piston 7.

This second, semi-cylindrical outer portion 10 carries at its front end two radially extending wings 11 and 12 substantially parallel to the sides 5a and 5b of the plate 5 and constituting the second bearing surface.

The wings 11 and 12 are interconnected by a ring segment 13 retaining this second semi-cylindrical portion 10 on the syringe body 1. When fitted to the syringe the assembly 7,8,9,10,11,12 and 13 constitutes a single rigid member.

Figure 3:
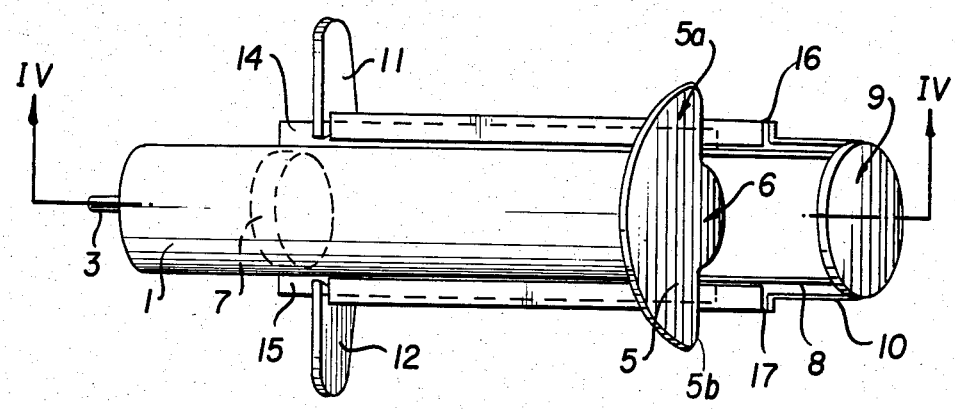
FIG. 3 illustrates in perspective view the second form of embodiment of the invention.
Figure 4:
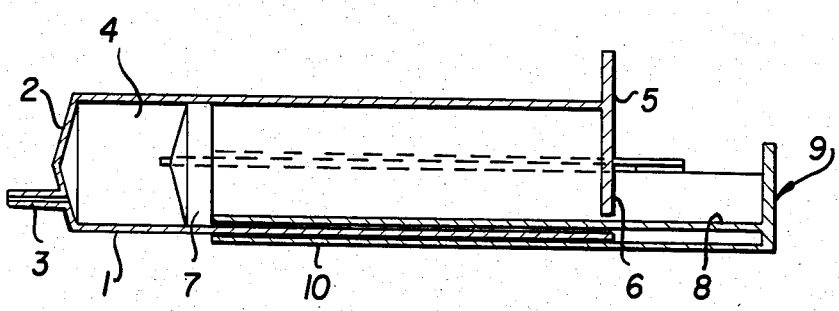
FIG. 4 is a longitudinal section taken along the line IV—IV of FIG. 3.

In the modified form of embodiment illustrated in FIGS. 3 and 4 of the drawings the ring segment 13, which in the first form of embodiment can only be fitted in position after the piston has been properly introduced into the cylindrical body 1, is replaced by a sliding guide system.

This system comprises on the one hand a pair of diametrally opposed longitudinal shoulders 14 and 15 formed integrally with the outer cylindrical portion of the syringe body 1 and on the other hand a pair of longitudinal U-shaped bent portions 16 and 17 opening inwardly and slidably engaged by said shoulders. In this case, the piston assembly 7,8,9,10,11,12,16,17 can be detachably fitted in and on the cylindrical body 1 formed with the retaining shoulders 14 and 15 of the guide system, in case the semi-circular extension 6 is either fitted in position afterwards or simply dispensed with.

To simplify the description of the mode of operation of the syringe in either of these two forms of embodiments, reference will now be made to FIGS. 5 and 6 in which the first bearing surface 5 is designated by the reference symbol A1, the second bearing surface being A2 and the third bearing surface A3. In the example illustrated, the operator holds the syringe in his or her right hand, with the thumb P, the forefinger I and the middle finger M.

In FIG. 5, the syringe is shown in its fluid taking function, the forefinger I and the middle finger M exerting a pressure against the front faces of the wings of the second bearing surface A2. The thumb P reacts against the rear face of the first bearing surface A1. By moving the forefinger and middle finger toward the thumb, the piston 7 (see FIGS. 1 or 3) is moved away from the closed end 2 of body 1 and thus the volume of the inner chamber 4 (see FIGS. 2 or 4) increases, thus sucking the fluid into the chamber. This operation, following a normal puncture made by driving a needle into a body (not shown), is usually referred to as a fluid taking operation.

FIG. 6 illustrates the emptying operation (which could also be an injection). In this case, the operator has simply transferred his thumb P from the first bearing surface A1 to the third bearing surface A3, and subsequently his forefinger I and middle finger M from the second bearing surface A2 to the first bearing surface A1.

The thumb, during its movement towards the forefinger and middle finger, causes the piston to be driven into the syringe body, thus reducing the volume of the chamber by ejecting the liquid contained therein through the nozzle 3 for example into a container in which the liquid is stored.

It will be seen that the operator needs only one hand for changing from the taking operation to the emptying operation.

Referring now to FIG. 7, the differences existing between the first and second form of embodiment, on the one hand, and the third form of embodiment, on the other hand, will become obvious. In this Figure, the reference symbols of FIG. 2 are used with the addition of a prime (') sign.

Rings or loops 18 and 19 are formed integrally with the front portion of wings 11' and 12'. In a modified version, the wing and ring assembly could be replaced by a single ring. Formed integrally with the rear portion of the first bearing surface 5' is a loop 20 which, if desired, could be replaced by a ring. These loops, intended for the thumb 20 and the forefinger and middle finger 18 and 19 respectively, could also consist of different forms of cavities or recesses permitting an alternating movement of the fingers toward and away from each other, as will be disclosed with reference to the next Figures, in which only the first and second bearing surfaces A1 and A2 are used for the taking and emptying functions, so as to improve the rigidity of the portions 8' and 10' of the piston rod, which is already appreciably increased by the presence of the end plate 9'. Furthermore, a stiffening weld seam 21 may be provided without interfering with the axial strokes of assembly 5', 6 and 20.

In the fluid-taking operation (FIG. 8) the syringe is used in the same manner as disclosed hereinabove with reference to FIG. 5. However, the thumb P is inserted in loop 20 and the middle finger and forefinger M and I are inserted in loops 18 and 19, respectively.

FIG. 9 illustrates the emptying operation. In this case, the position of the operator's fingers is unchanged, as in the case illustrated in FIG. 6 and described hereinabove. The only difference is that, after moving the forefinger and middle finger toward the thumb for taking fluid (FIG. 6), the operator moves the forefinger and middle finger away from the thumb, these three fingers being retained by the loops 18, 19 and 20. When the piston is properly lubricated, this finger separation is accomplished without any difficulty.

The syringe according to the instant invention is attended by several advantageous features. Thus, in its usual version for one use only (throw-away syringe) it can be manufactured as easily and economically as any hitherto known throw-away syringe.

During the puncture (introducing the syringe needle into the patient's body) the forefinger and middle finger of the practitioner's hand are very close to the needle without interfering with this step while affording a good degree of precision of the needle driving movement.

Then, the fluid to be taken is sucked with a maximum precision and a good finger-touch, while permitting a correction or a modification of the puncture proper, if necessary. In fact both guiding and suction are controlled simultaneously by using only one hand.

Any jamming of the piston in the cylindrical body is positively prevented by the mutual sliding engagement between these two component elements. Besides, the fact that the syringe can be actuated single-handed prevents the piston from escaping from the cylindrical body at the end of its stroke.

The sliding engagement between the cylindrical body and the piston also avoids any overhang detrimental to the operation.

Finally, it is a very important feature of the present invention that the practitioner or the operator constantly keeps a free hand, since the syringe is operated single-handed in all its functions. This free hand is extremely valuable, for instance in the case of nervous children or patients, or for simultaneously combining the fluid-taking operation with other useful movement or operations.

What is claimed is:

1. Syringe for extracting and emptying a liquid comprising:
    a cylindrical body provided on its close front end with a needle supporting nozzle, and a piston movable coaxially in said body so that a relative axial movement between the body and the piston will correspond to a variation in the volume of the chamber formed between the front end of the body, its cylindrical wall and the adjacent surface of the piston for sucking or ejecting a liquid through said needle supporting nozzle, wherein the body comprises at its rear end a first bearing surface and that the piston is rigid through its rod, being coaxial and approximately semi-cylindrical cross-section, with a second bearing surface located between the first bearing surface and the front end of said body, so that when the second bearing surface is moved toward the first bearing surface the volume of the inner chamber increases, whereas when said second bearing surface is moved away from the first bearing surface the volume of said chamber decreases, the piston rod comprises a first inner part and a second outer part, being of approximate semi-cylindrical cross-section, connected at their rear end to a terminal part, whereby the inner part is fixed to the piston and the front end of the outer part is fixed to the second bearing surface.

2. Syringe according to claim 1 wherein the first bearing surface comprises a central portion on the rear part of which the thumb of the user's hand is adjusting, and by the fact that the second bearing surface is formed of two opposed radially extending wings on the front surface of which the forefinger and the medium finger of the user adjust, all this providing for the single hand use of the syringe in its extracting function by pinching together the fore and medium fingers with the thumb, wherein the forces transmitted by the fingers of the user on the opposed bearing surfaces produce a resulting force substantially parallel and confounded with the main syringe axis.

3. Syringe according to claim 1 wherein the first bearing surface comprises on both sides of its central portions diametral extensions which are parallel and approximately symmetrical with regard to the wings of the second bearing surface and by the fact that the third bearing surface has a central portion paralle to, and approximately symmetrical with that of the first bearing surface, the arrangement providing for the single hand use of the syringe both in its first extraction function and in its second emptying or injection function, the thumb of the user coming to bear successively on the central portion of the first bearing surface and on the central portion of the third bearing surface while the fore- and index fingers of the same hand of the user bear successively on the front part of the wings of the second bearing surface and on the front part of the radial extensions of the first bearing surface and working the syringe, in its second function, by pinching together the thumb with the fore- and index fingers.

4. Syringe according to claim 1 wherein a ring segment closes the second outer semi-cylindrical part of the piston rod around the cylindrical body, so that this second part may slide along the body without being separated from it.

5. Syringe according to claim 1 wherein it comprises two diametrically opposed longitudinal shoulders on the outer side of the cylindrical body and two longitudinal U-shaped portions on the outer semi-cylindrical part of the piston rod in sliding relationship with said shoulders, so that said outer part may more relative to the body without risking to separate from it.

6. Syringe according to claim 1 wherein it comprises two diametrically opposed longitudinal grooves in the outer part of the cylindrical body and two longitudinal folded edges of the outer semi-cylindrical part of the piston rod entering said grooves so that the rod may slide on the body without risking to separate from it.

7. Syringe according to claim 1 wherein the first bearing surface has an inner radial extension so that the thumb of the operator's hand may bear on said surface along or substantially along the piston axis.

8. Syringe according to claim 1 wherein the first bearing surface shows on its rear end a first annular recess and by the fact that the second bearing surface is formed of two opposed radially extending wings on the front parts of which are provided two second annular recesses, all this making it possible to operate the syringe single-handed, the thumb of the hand being placed in the first recess and the fore- and middle fingers being placed in the second recesses so that by moving the fore- and middle fingers towards the thumb the volume of the chamber increases for intaking of liquid whereas by moving the fore- and middle fingers away from the thumb the volume of the chamber decreases for emptying or injection purposes.

* * * * *